United States Patent [19]

Ambrus et al.

[11] Patent Number: 4,612,122
[45] Date of Patent: Sep. 16, 1986

[54] REMOVING HEAVY METAL IONS FROM BLOOD

[76] Inventors: Clara Ambrus; Csaba Horvath, both of 225 Franklin St., Boston, Mass. 02110

[21] Appl. No.: 650,772

[22] Filed: Sep. 13, 1984

Related U.S. Application Data

[63] Continuation-in-part of Ser. No. 473,814, Mar. 9, 1983, abandoned, which is a continuation-in-part of Ser. No. 278,631, Jun. 29, 1981, abandoned.

[51] Int. Cl.4 ............................................. B01E 13/00
[52] U.S. Cl. ..................................... 210/638; 210/927
[58] Field of Search .................. 210/638, 321.1, 321.2, 210/321.3, 651, 927

[56] References Cited

U.S. PATENT DOCUMENTS

| 3,872,001 | 3/1975 | Davis et al. | 210/638 |
| 3,957,504 | 5/1976 | Ho et al. | 210/638 X |
| 4,247,393 | 1/1981 | Wallace | 210/638 |
| 4,266,026 | 5/1981 | Breslau | 210/638 X |
| 4,437,994 | 3/1984 | Baker | 210/638 |

OTHER PUBLICATIONS

Maher et al., "The Dialysis of Poisons and Drugs", from *Tsasalo*, vol. XIV, published 6-14-68, pp. 440-453.

*Primary Examiner*—Frank Spear
*Attorney, Agent, or Firm*—Andrew F. Kehoe

[57] ABSTRACT

Apparatus and process of removing quantities of heavy metals from blood utilizing immobilized chelating agents which are positioned on the opposite side of an anisotropic membrane from blood flowing across the retentive filter surface of the membrane.

7 Claims, 3 Drawing Figures

REMOVING HEAVY METAL IONS FROM BLOOD

RELATED APPLICATION

This application is a continuation-in-part of copending U.S. patent application Ser. No. 473,814, filed Mar. 9, 1983 which in turn was a continuation-in-part of its copending U.S. patent application Ser. No. 278,631 filed on June 29, 1981 by Clara M. Ambrus and Csaba G. Horvath, both now abandoned.

BACKGROUND OF THE INVENTION

This invention relates to a process for removing toxic quantities of heavy metals from the bloodstream and membrane apparatus for use in the process. It is already known that substantial health problems are encountered by those who build up excessive amounts of heavy metal within their bodies. Particularly well known toxic metals which are often present in contaminated environments are iron, cadmium, lead, radioactive metals, and mercury. However, physiological disorders can result in a patient building up toxic quantities of metals (iron-copper) in the bloodstream even when the environment is normal.

Many methods of treatment for heavy-metal poisoning are based on the use of specific agents which convert the metal to a chemical form in which it is relatively inert and can be readily excreted. Such treatments take time and are quite specific and, consequently, depend excessively on a precise diagnosis. They are more time consuming than is desirable.

As described below, the present invention is intended to overcome some of these problems.

Also, outer pore surface of membranes have been used to hold chemicals and catalysts by Breslau in U.S. Pat. No. 4,266,026 and various prior work cited by him in his patent. In all of this prior work, a relatively conventional flow of material through the membrane barrier layer was realized before any component within the lumen of the membrane is reacted with a catalyst or other reactant carried in the large pores.

Introduction of various chelating agents into the bloodstream of mammals has been suggested in a number of such references including several set out in the extensive bibliography attached to an article entitled *"The Dialysis of Poisons and Drugs"* by John F. Maher and George E. Schreiner in Volume XIV of the American Society for Artificial Internal Organs; 1968, pages 440–453. One of many such articles are those relating to canine iron intoxification and to peritoneal dialysis of a patient with ferrous sulfate poisoning, all referred to at page 445 of the above-identified article. Other articles, such as Looney et al (reference in the above-identified Maher et al reference) describe direct contact of blood, including the formed elements with the chelating material. This procedure results in undesirable absorption or rupturing of the platelets, i.e. thrombocytes. As indicated above, side effects of such direct contact with the bloodstream have prevented these procedures from becoming of general therapeutic value. Moreover like most direct chemical treatment, use of chelating agents in this way can itself cause undesirable toxic reactions, particularly to patients already weakened by metal poisoning.

OTHER ART

Still more recently U.S. Pat. No. 4,361,484, published after the invention was made by Applicants, utilized relatively large holes in membranes and varied pressure to pull blood components into and out of the membrane and achieve removal of some blood components. That patent disclosed use of pores "preferably 0.15 to 0.45 micron" through which the blood components could move, that is flow, to contact a biologically active material on the outside of the membrane. Hydraulic means to augment the flow was necessary for practice of the invention.

SUMMARY OF THE INVENTION

It is a principal object of the present invention to provide an improved process for removal of heavy metal ions from blood, one that does not depend on hydraulic phenomena, but on selective diffusion of ions through a membrane barrier.

Another object of the invention is to provide an improved apparatus for carrying out the process.

Other objects of the invention will be obvious to those skilled in the art on reading this disclosure.

The above objects have been substantially achieved by construction and use of a process in which blood to be purified is passed over an anisotropic membrane which is in intimate contact on the non-blood-wetted side of the membrane with a non-proteinaceous chelating agent which forms means to accept and immobilize heavy metal ions at substantially greater density, higher rates and lower cost than proteinaceous "antibodies". The chelating agent is not bound to the membrane.

Applicants have discovered that very small pores may be used in this work, i.e., pores having a nominal 50,000 molecular weight cut-off. Such pores have only effective pore sizes of about 0.001–0.002 microns. Surprisingly, despite this pore size and the relative resistance of such pore size to any artificial flow-stimuli, the metal cations can still find their way to the pore sites that a properly-packed, chelate-filled pore structure will be able to seize metal ions from the blood. This phenomena is best called diffusion. It does not require a liquid flow for carrying the cations into proximity to the chelate. Any liquid in the membrane is substantially static and functions only as a diffusion path for the cations.

The membrane is preferably an anisotropic membrane with the tight or retention side facing the bloodstream. Such membranes are most commonly used in ultrafiltration processes, and are commercially available. The membrane is conveniently formed of any number of polymers known to the art. The degree of blood compatibility of the membrane need not be high, because the apparatus will usually be discarded or cleaned after anything from a few minutes to a few hours of service. Nevertheless, some attention should be given to avoiding use of surfaces which are known to interact unfavorably with blood and have no particular benefit for the application being described.

One membrane that is suitable for use is the polysulfone membrane sold by Amicon Corporation under the trade designation P10. It is the membrane that is used in Amicon's HIP10 ultrafiltration module. That membrane has a nominal molecular weight retention rating of 10,000.

One way of further increasing the intimacy with which the chelating resin is in contact with the membrane is to circulate a slurry or solution of the chelating agent rather than have a relatively static mass in contact with the membrane. It is also possible to utilize liquid chelating macromolecules that cannot pass through the membrane that are in static or dynamic contact with the opposite side of the membrane from the physiological fluid being processed.

Surprisingly, the immobilized chelate is so efficient that there is little additional value to employing this recirculation technique.

It has been found that, even though some quantity of a toxic metal atom will be carried on organic molecules which are large enough to be retained in the bloodstream, a significant number of metal atoms are in equilibrium with smaller compounds. As these smaller molecules or metal ions permeate the membrane the metal ion can be captured by the chelating agent, the equilibrium reestablishes itself to assure the availability of still additional metal ions to the chelate. This procedure continues until the concentration of metal in the blood is substantially reduced, i.e. reduced to a physiologically tolerable level. In many instances, it is possible to reduce the concentration of metal to acceptable levels within minutes. Occasionally, the limiting factor in the removal procedure will be gradual rate of removal of the ion from a patient's tissue into the bloodstream. Treatment of several hours or for short periods spaced over a period of several days or weeks may be desirable in such a situation. Among the heavy metals which can be removed by a typical multivalent chelating agent are mercury, copper, nickel, cobalt, zinc, iron, cadmium, lead, uranium, manganese, berylium and plutonium.

Multi-valent chelating agents are preferred for use in the invention. The chelating resin which is used should be in a neutralized form. Chelating ion exchange resins are advantageously used. The sodium form of a material sold under the trade designation Chelex 100 by BI0-Red Laboratories is useful when properly prepared and intimately contacted with the membrane as will be described below.

Among other chelating agents that can be immobilized in the porous outer structure of the membrane are imonoacetic acid derivatives such as (EDTA) and diethylene triaminepenta acetic acid (DTPA), hydroxamic acids of natural origin such as deferoxamine and rhodotorulic acid. When the chelating agent is itself a liquid, it is most convenient and most efficient to use it on a substrate of silica gel, dextran, or the like.

The use of an anisotropic membrane has a number of advantages. Undesirable contact interaction between the solid resin and the formed elements of the blood is eliminated and the desired ion transport is maximized with a minimum effect on the blood by the chelating resin.

It is preferable that the membrane be used in the tubular form in order to facilitate the maintenance of appropriate flow velocities, and flow distribution, of blood over the membrane surface. Velocities that are too high, even locally, can result in excessive damage to the blood, especially to the blood platelets. On the other hand, velocities that are too low tend to reduce the efficiency of the ion removal and prolong the time needed for treatment. In general, velocities known to the blood processing art, e.g. those used in dialysis are suitable for use in the process of the invention.

Anisotropic membranes, i.e. those having a very thin barrier layer in contact with the blood and a more porous substructure as a support are particularly useful in the process of the invention for they allow the chelating resin to be brought into intimate contact with the thin barrier membrane, impregnated well into the more grossly porous substructure of the membrane. Indeed, this a particularly desirable configuration of the invention.

To facilitate this packing, the chelating resin is reduced to a paste or slurry which can be caused to pack closely around the exteriors of closely packed membranes in parallel with one another.

Flow rates may vary widely, e.g. between about 0.03 ml per minute to about 3 ml per minute per ultrafilter tube. Rates between 1 and 2 ml per minute are preferred. These preferred rates indicate average linear blood flow from about 20 to about 100 ml per minute through the Amicon P10 tubular ultrafilter.

Although, it is feasible to process whole blood using the process of the invention, it is also possible to utilize other physiological fluids. For example, blood fractions may be processed when, for some reason, this is appropriate for removal of a particular metal.

The nominal retention values of a membrane which are referred to herein are known in the art to be appropriately determined with dilute solutions of standard materials, for example a dextran polymer in 0.1% solution of the type sold under the trade designation "Blue Dextran".

The system, once it reaches equilibrium, is virtually free of any liquid flow through the membrane. Depending on the relative moisture content of the chelate-bearing substance to start up, water will seep rapidly from the blood to the chelate side. Thereafter, the water primarily serves to provide a diffusion path for the cation through the membrane structure to the chelation sites. The membrane structure itself does not function as an ultrafilter but only as a "diffusion barrier" allowing cation diffusion through the barrier layer and preventing diffusion of the larger blood components.

The range of nominal molecular weight retention values will be from about 10,000 to 50,000. This range depending upon the metal ion being removed, is selected to prevent liquid flow through the membrane while allowing diffusion to the cations of interest for a particular application. The one favored chelating agent is a macromolecular, organic substance containing iminodiacetate or hydroxamid acid groups. These materials—as opposed to proteinaceous materials—allow a relatively large concentration of active cation-receptive sites in the membrane pores. The materials are conveniently resins. They may be liquids. If such liquids are not immobilized on a substrate like silica gel, the molecular weight must be such as to prevent any diffusivity of the chelate to the blood side of the membrane.

IN THE DRAWINGS

ILLUSTRATIVE EXAMPLE OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for the purposes of illustration in order that others skilled in the art will more fully understand the invention and the principles thereof and will be able to modify it and embody it in a variety of forms, each as may be best suited to the condition of a particular case.

Figure 1:
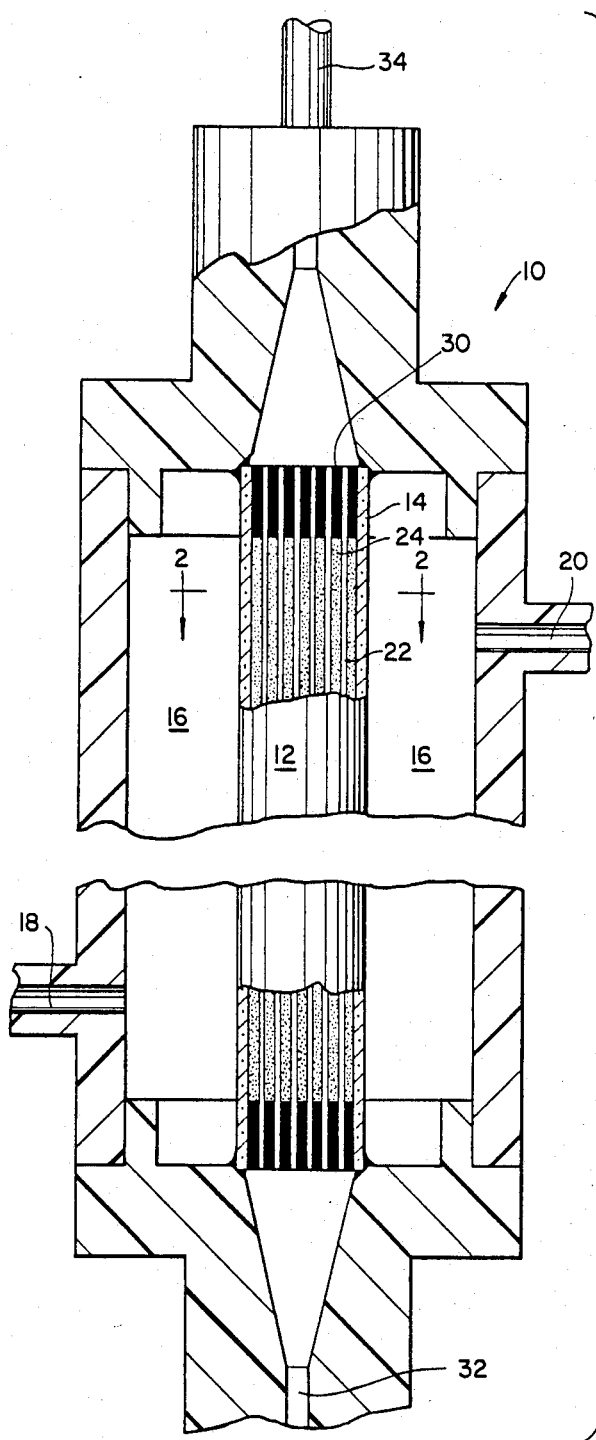
FIG. 1 is a partially schematic view of an apparatus useful in the practice of the invention.
Figure 2:
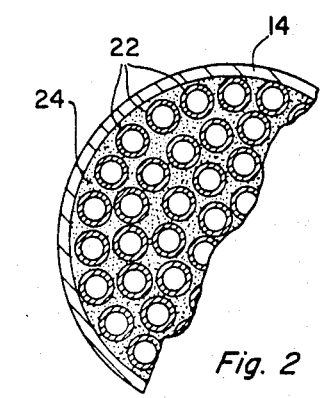
FIG. 2 is a section of FIG. 1.

Referring to FIG. 1, it is seen that a blood processing cartridge 10 is formed of an interior, blood-processing chamber 12 formed of interior glass wall 14. Around chamber 12 is an exterior chamber 16 which is utilized to control the temperature in chamber 12; the temperature of which is kept constant. A temperature-controlling fluid is passed into chamber 16 through lower conduit 18 and passes out of the chamber through upper conduit 20. Chamber 12 contains about five hundred tubular, anisotropic, ultrafiltration membranes 22 of the type generally called "hollow-fiber membrane". In fact, these membranes are about 0.3 millimeters in inside diameter and 0.5 millimeters in outside diameter. They have interior retentive membrane walls of about 1 micron in thickness and have a nominal central conduit path of about 8 inches.

The membranes are sealed together in matrices of resin 30 at the inlet port 32 outlet port 34. The resin effectively seals any crossectional area which may be left between the membranes and assures that all blood entering the apparatus through inlet 32 flows into the tubular membranes 32.

Around membranes 22 is a mass chelating resin 24. In a typical experiment to demonstrate the effectiveness of the device about 100 ml per minute of blood is permitted to flow through the 70 tubes for a period of 60 minutes. The iron content of the plasma is reduced from 50 mg. percent to 3 mg. percent in 3 passes. Most of the iron is removed from the plasma in about 3 minutes. Similar results are achieved with other heavy metals.

PURIFICATION OF SHEEP BLOOD-COPPER

A 50-kilogram, male sheep was injected intramuscularly with 125 milligrams of copper in the form of 500 milligrams of copper sulfate. A diffusion-purification apparatus according to the invention as described herein was connected from artery to vein of the sheep, and blood was shunted therethrough. After the injection, and before connecting the purifying apparatus, the copper cation concentration in the blood of the sheep was 240 micrograms per deciliter. After 30 minutes of circulation through the apparatus of the invention the concentration dropped to 180; after 30 more minutes of such circulation, the level dropped to 110 milligrams of copper ion per deciliter of sheep blood. A total of at least 4500 micrograms of copper was removed from the blood in 60 minutes.

PURIFICATION OF SHEEP BLOOD-LEAD

The same general procedure was followed in preparing another male sheep. The sheep weighed 48 kilograms and was injected with 2 grams of lead nitrate, i.e. Pb(NO$_3$)$_2$. The initial lead level in the sheep's blood was 120 micrograms per deciliter. This dropped to 82 micrograms in 30 minutes and to 10 micrograms in the next 30 minutes. At least 3400 micrograms of lead was removed in 60 minutes.

CONCURRENT REMOVAL OF CATIONS FROM BLOOD

A blood sample was prepared having initial concentrations of the following quantities of metals:
Iron—0.001837 grams per deciliter
Copper—0.002040 grams per deciliter
Lead—0.000804 grams per deciliter
The blood was circulated at 100 ml per minute for sixty minutes through a purifier as described herein. The levels after 60 minutes, were
Iron—975 (53%) grams per deciliter
Copper—1272 (62%) grams per deciliter
Lead—432 (54%) grams per deciliter
Thus the levels of removal from the single blood samples were 47%, 38% and 46% for iron, copper and lead respectively.

PREPARATION OF THE CHELATING RESIN

One suitable way of preparing the chelating resin for use is illustrative:

The commercial resin, Chelex 100, was vacuum dried at 80° C. for 24 hours. The dry particles of resin were ballmilled to obtain a fine powder having an average particle size of about 5 microns in diameter. The power should be below 10 microns in diameter.

A quantity of 249 grams of the powder was washed with 500 ml of one normal HCl in which it was allowed to soak, washed in water, washed with 500 ml of 1.0 normal sodium hydroxide in which it was allowed to soak for 24 hours before being given a final wash with 1000 ml of distilled water. These washings were such that, after each washing, the solid material was allowed to settle and the supernatant liquid was decanted. Before the settling step following the last wash, suspended solids were neutralized with 1 normal HCl.

The material remaining was a paste which, upon being dried at 100° C. yielded 0.17 grams of dry Chelex 100 powder per gram of wet paste.

The cartridge was prepared by slurrying it in water and sucking the slurry into the shell through those spaces existing between the tubes mounted in place within the shell. It was found desirable to shake or vibrate the apparatus during the filling procedure. This aided the obtaining of intimate contact between the outer walls of the membranes and the slurry particles. Also, from time to time, water was added to help redistribute some of the resin particulate matter. After filling the residual moisture was removed by vacuum drying before the tubes were sealed for storage or shipment.

A total of about 3 grams of chelating resin was left on the exterior of the membrane surfaces.

Figure 3:
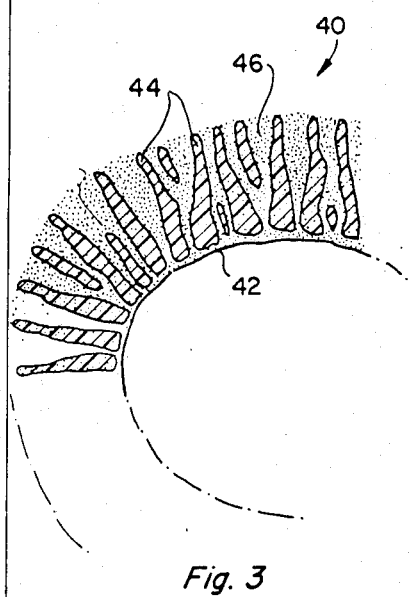
FIG. 3 is a greatly enlarged cross-section of a hollow-fiber membrane structure constructed according to the invention.

Referring to FIG. 3, it is seen that a hollow fiber membrane structure 40 is composed of a single polymeric material which is formed into a tubular section comprising a relatively tight, very thin ultrafiltration membrane 42 and relatively porous, exterior structure 44. In the pores 44 have been immobilized chelating agent 46 such as, e.g. a poly(dicarboxylmethyliminomethyl)styrene resin compound or macromolecular liquid chelating agent.

It is also to be understood that the following claims are intended to cover all of the generic and specific features of the invention herein described and all statements of the scope of the invention which might be said to fall therebetween.

What is claimed is:

1. A process for removing heavy metal ions from blood fluid comprising the steps of passing such fluids along the retentive barrier side of an anisotropic membrane and, while preventing any substantial liquid flow through the membrane, allowing said ions to diffuse through said membrane into contact with a mass of ion-capturing means which is in a closed container and at least partially immobilized within the porous substrate at the opposite side of said membrane from said blood, said mass being an organic chelating agent powder; wherein said membrane has a maximum nominal molecular weight retention value of about 50,000 and wherein said closed container, on being initially filled with liquid, forms means to prevent liquid flow through said membrane and to assure only diffusion of said metal cations through said membrane.

2. A process as defined in claim 1 wherein said chelating resin is a finely-divided, multi-valent carboxylate salt-bearing resin.

3. A process as defined in claim 1 wherein said physiological fluid in blood or a fraction of blood and wherein said membrane surface in the form of a plurality of tubes around which said agent is placed.

4. Apparatus for removing heavy metal ions from blood fluid comprising an anisotropic membrane of the type having a retentive skin and a porous substrate and forming a diffusion barrier means permeable to water and some heavy metal cations diffusible through said water but substantially impermeable to formed elements of said blood fluid, a flow path forming means for directing said fluid to contact the retentive skin of said membrane, and, retained within a closed container and, at least partially within said porous support structure of said membrane a mass of chelating agent powder; wherein said powder is below 10 microns in average particle size and where said membrane has nominal molecular-weight retention value below about 50,000 and wherein said closed container, on being initially filled with liquid, forms means to prevent liquid flow through said membrane and to assure only diffusion of said metal cations through said membrane.

5. Apparatus as defined in claim 4 wherein said chelating resin is a finely-divided, multi-valent resin composition.

6. Apparatus as defined in claim 5, wherein said chelating resin comprises multi-valent carboxylate groups thereon.

7. Apparatus as defined in claim 4, wherein said retention value is about 10,000.

* * * * *